(12) United States Patent
Woo et al.

(10) Patent No.: US 7,440,796 B2
(45) Date of Patent: Oct. 21, 2008

(54) SYSTEM AND METHOD FOR THREE-DIMENSIONAL VISUALIZATION OF CONDUCTIVITY AND CURRENT DENSITY DISTRIBUTION IN ELECTRICALLY CONDUCTING OBJECT

(75) Inventors: Eung Je Woo, Seongnam-si (KR); Jin Keun Seo, Seoul (KR); Ohin Kwon, Seoul (KR)

(73) Assignee: Kohwang Foundation, Kohwang Board of Trustee, Seoul (KR)

( * ) Notice: Subject to any disclaimer, the term of this patent is extended or adjusted under 35 U.S.C. 154(b) by 21 days.

(21) Appl. No.: 10/541,719

(22) PCT Filed: Dec. 24, 2003

(86) PCT No.: PCT/KR03/02825

§ 371 (c)(1),
(2), (4) Date: Apr. 14, 2006

(87) PCT Pub. No.: WO2004/062464

PCT Pub. Date: Jul. 29, 2004

(65) Prior Publication Data

US 2006/0224061 A1    Oct. 5, 2006

(30) Foreign Application Priority Data

Jan. 10, 2003  (KR)  .................. 10-2003-0001622
Jun. 25, 2003  (KR)  .................. 10-2003-0041569

(51) Int. Cl.
*A61B 5/05* (2006.01)

(52) U.S. Cl. ..................... 600/547; 600/411
(58) Field of Classification Search ............... 600/410, 600/411, 547, 549
See application file for complete search history.

(56) References Cited

U.S. PATENT DOCUMENTS

| 5,465,730 | A | 11/1995 | Zadehkoochak | |
| 6,397,095 | B1* | 5/2002 | Eyuboglu et al. | 600/411 |
| 6,501,984 | B1 | 12/2002 | Church | |
| 2007/0088210 | A1* | 4/2007 | Woo et al. | 600/410 |

* cited by examiner

*Primary Examiner*—Eric F Winakur
*Assistant Examiner*—Michael T. Rozanski
(74) *Attorney, Agent, or Firm*—Workman Nydegger

(57) ABSTRACT

System for visualizing conductivity and current density distributions including a plurality of current injecting devices for injecting currents into a measuring object, an MRI scanner for measuring one directional component of a magnetic flux density due to each of the currents injected into a measuring object, an operating part for controlling the current injecting devices so as to inject currents of different directions into the measuring object, and calculating a conductivity distribution and a current density distribution inside of the measuring object by using the one directional component of a magnetic flux density, and displaying means for visualizing the conductivity and current density distributions calculated by the operating part, thereby permitting to visualize the conductivity and the current density of the measuring object more accurately.

8 Claims, 4 Drawing Sheets

SYSTEM AND METHOD FOR THREE-DIMENSIONAL VISUALIZATION OF CONDUCTIVITY AND CURRENT DENSITY DISTRIBUTION IN ELECTRICALLY CONDUCTING OBJECT

TECHNICAL FIELD

The present invention relates to system and method for visualization of conductivity (or resistivity) and/or current density distributions of a measuring object, such as a human body, or a substance.

BACKGROUND ART

In general, X-ray, MRI, or ultrasound is used in visualization of an inside structure of the human body or the substance. However, the methods can not visualize electrical properties of the human body or the substance.

As an effort for solving the problem, a method for visualizing current density distribution of an inside of a measuring object using the MRI is initially suggested by a research team of the Toronto University in 1989, and, thereafter, there have been active researches related thereto. This is the Current Density Imaging (CDI) technique.

In the present CDI, a magnetic flux density B due to an injected current I is measured by using MRI technique, and a current density J is calculated by using the Ampere's law $$J = \frac{1}{\mu_0} \nabla \times B,$$

for visualizing an inside current density distribution.

However, the CDI has a drawback in that rotation of the measuring object in an MRI scanner is required for obtaining the magnetic flux density B having three components Bx, By, and Bz. This is because the MRI scanner can only measure a z-directional component, a direction the same with a main magnetic field, of the flux density, i.e., Bz, when the measuring object is in the MRI scanner.

That is, since the component the MRI scanner can measure at a time is only the Bz component, for obtaining all the required three components of the magnetic flux density vector, the present CDI technique has a serious drawback of requiring the measuring object (the human body, or the substance) to be rotated in the MRI scanner.

Meanwhile, as a known method for visualizing the electrical properties of the human body, or the substance, there has been Electrical Impedance Tomography (EIT) that has been under active research starting from late 1970s. The EIT provides an image of resistivity (or conductivity) distribution, an electrical property of the measuring object.

In the EIT mostly taking the human body as the measuring object, many electrodes are attached on a surface of the human body, for visualizing the resistivity distribution of an inside of the human body.

The visualization of the human body according to the resistivity is made possible since tissues of the human body, such as blood, bones, lung, heart, and the like have electrical properties different from one another.

However, due to a fundamental drawback of the EIT, an image of the EIT is poor, to support only a low resolution. That is, EIT has a fundamental drawback in that a current-voltage data measured by EIT is extremely insensitive to variation of resistivity of an inside of the human body. Therefore, clinical application of EIT is difficult, presently.

Even if CDI is applied to EIT, because it is required to rotate the measuring object (the human body, or the substance), the technical drawback can not be resolved.

DISCLOSURE OF INVENTION

An object of the present invention, designed to solve the related art problem, is to provide system and method for visualization of conductivity and current density distribution, in which electrical properties (conductivity and current density) of a measuring object can be visualized in more accurate high resolution without rotating the measuring object.

The object of the present invention can be achieved by providing a system for visualizing conductivity and current density distributions including a plurality of current injecting devices for injecting currents into a measuring object, an MRI scanner for measuring one directional component of a magnetic flux density due to each of the currents injected into a measuring object, an operating part for controlling the current injecting devices so as to inject currents of different directions into the measuring object, and calculating a conductivity distribution and a current density distribution inside of the measuring object by using the one directional component of a magnetic flux density, and displaying means for visualizing the conductivity and current density distributions calculated by the operating part.

The current injecting device includes a current source and plurality of recessed electrode assemblies. Each recessed electrode assembly includes an electrode, an insulating container with the electrode attached at one side and an electrolyte substance inside, and a wire for supplying the current to the electrode.

The operating part calculates an inside voltage and a surface voltage of the measuring object for a first conductivity, and calculates a second conductivity by using the inside voltage and the measured one directional component of the magnetic flux density. The operating part multiplies or divides a constant to the second conductivity according to a ratio of a calculated surface voltage to a measured surface voltage.

The operating part determines that the second conductivity is a true conductivity, if an absolute value of a difference of the first conductivity and the second conductivity is smaller than a tolerance value, and if the absolute value of the difference of the first conductivity and the second conductivity is greater than the tolerance value, the operating part calculates the inside voltage and the surface voltage for the second conductivity, and calculates a third conductivity by using the inside voltage for the second conductivity and the measured one directional component of the magnetic flux density. This process repeats until the tolerance value is achieved.

In other aspect of the present invention, there is provided a method for visualizing conductivity and current density distributions including the steps of (a) injecting currents of different directions into a measuring object through current injecting devices attached to a surface of the measuring object, (b) measuring one directional component of a magnetic flux density of due to each of the currents injected into the measuring object, (c) calculating a conductivity and a current density of the inside of the measuring object by using the measured one directional component of the magnetic flux density, and (d) visualizing the conductivity and the current density.

The step (a) includes the steps of selecting a pair of the current injecting devices in succession, and injecting the currents into the measuring object in succession through the selected pair of the current injecting devices.

The step (c) includes the steps of calculating the inside voltage and the surface voltage of the measuring object for a first conductivity, and calculating a second conductivity by using the calculated inside voltage and the measured one directional components of the magnetic flux density.

The step (c) further includes the step of multiplying or dividing the second conductivity by a constant according to a ratio of the calculated surface voltage and a measured surface voltage of the measuring object, and further includes the steps of calculating an absolute value of a difference of the first conductivity and the second conductivity, and comparing the absolute value of the difference to a tolerance value.

The step (c) further includes the steps of determining the second conductivity being a true conductivity, if the absolute value of the difference of the first conductivity and the second conductivity is smaller than the tolerance value, and opposite to this, if the absolute value of the difference of the first conductivity and the second conductivity is greater than the tolerance value, the step (c) further includes the steps of calculating the inside voltage and the surface voltage of the measuring object for the second conductivity, and calculating a third conductivity by using the inside voltage and the measured one directional component of the magnetic flux density for the second conductivity.

BRIEF DESCRIPTION OF DRAWINGS

The accompanying drawings, which are included to provide a further understanding of the invention, illustrate embodiment(s) of the invention and together with the description serve to explain the principle of the invention. In the drawings.

BEST MODE FOR CARING OUT THE INVENTION

Figure 1:
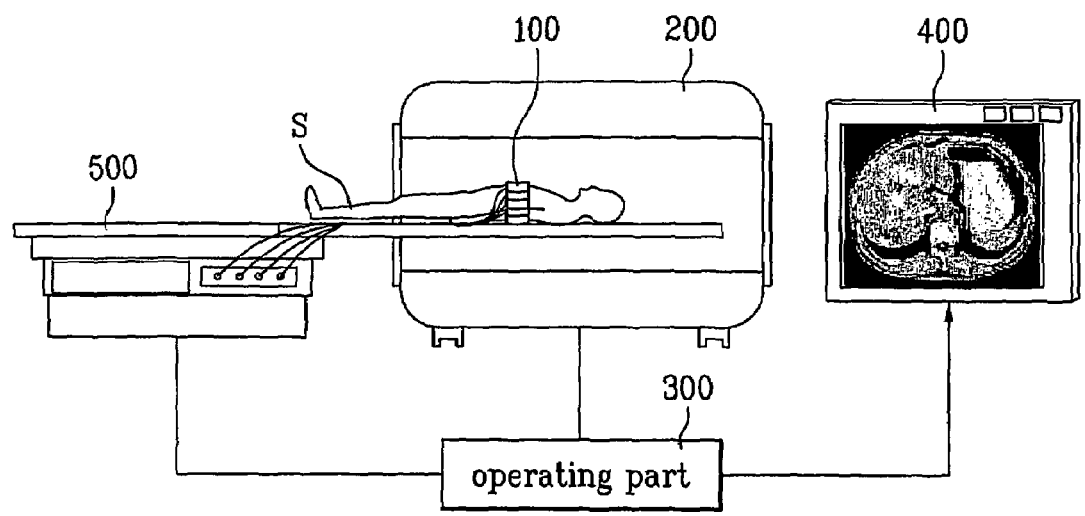
FIG. 1 illustrates a diagram of a system for visualizing conductivity and current density distribution in accordance with a preferred embodiment of the present invention.

Reference will now be made in detail to the preferred embodiments of the present invention, examples of which are illustrated in the accompanying drawings. In describing the embodiments, same parts will be given the same names and reference symbols, and repetitive description of which will be omitted. FIG. 1 illustrates a diagram of a system for visualizing conductivity and current density distribution in accordance with a preferred embodiment of the present invention.

Referring to FIG. 1, the system for visualizing conductivity and current density distributions includes current injecting devices 100 for injecting currents in directions different from one another into a measuring object, such as a human body or a substance, an MRI scanner 200 for measuring a magnetic flux density due to each of the currents, an operating part 300 for calculating a conductivity (or resistivity) distribution and a current density distribution inside of the measuring object from the currents and the magnetic flux densities induced thereby, displaying means 400 for displaying the inside of the measuring object as an image of the conductivity and current density distributions, and a current source 500 for supplying the currents to the current injecting device 100.

Figure 2:
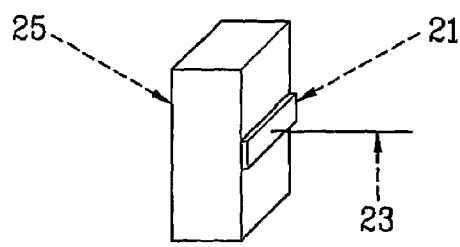
FIG. 2 illustrates a diagram showing a current injecting device in FIG. 1 in accordance with a first preferred embodiment of the present invention.

The current injecting device 100 includes an electrode 21 formed of a non-magnetic metal, such as copper, or a material having very high conductivity, and a wire for supplying the current to the electrode 21. Though direct attachment of the electrode 21 to a surface of the measuring object is possible, it is preferable that the electrode 21 is spaced apart from the surface of the measuring object for preventing distortion of the magnetic flux density at the surface of the measuring object. Therefore, as shown in FIG. 2, one embodiment of the current injecting device 100 of the present invention further includes an insulating container 25 having the electrode 21 attached thereto for putting the electrode 21 on a place spaced apart from the measuring object. The insulating container 25 has one surface having the electrode 21 attached thereto, and the other surface to be brought into contact with the measuring object in an opened state. The insulating container 25 is stuffed with sponge having an electrolyte gel or electrolyte solution absorbed therein. The sponge having an electrolyte gel or electrolyte solution absorbed therein makes uniform flow of the current from the electrode 21 in the insulating container 25. Thus, by putting the electrode on a place spaced apart from the surface of the measuring object by using the insulating container 25, and supplying the current to the measuring object uniformly by using the sponge having the electrolyte gel or electrolyte solution absorbed therein, distortion of an MRI image at the surface of the measuring object in contact with the electrode 21 can be reduced.

Figure 3A:
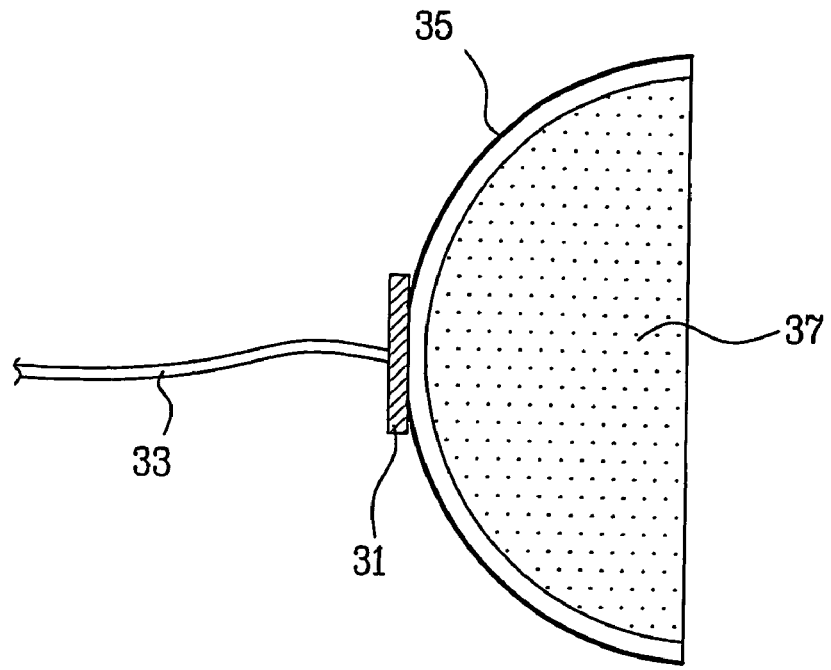
FIGS. 3A and 3B illustrate diagrams each showing another embodiment of the current injecting device in FIG. 1.
Figure 3B:
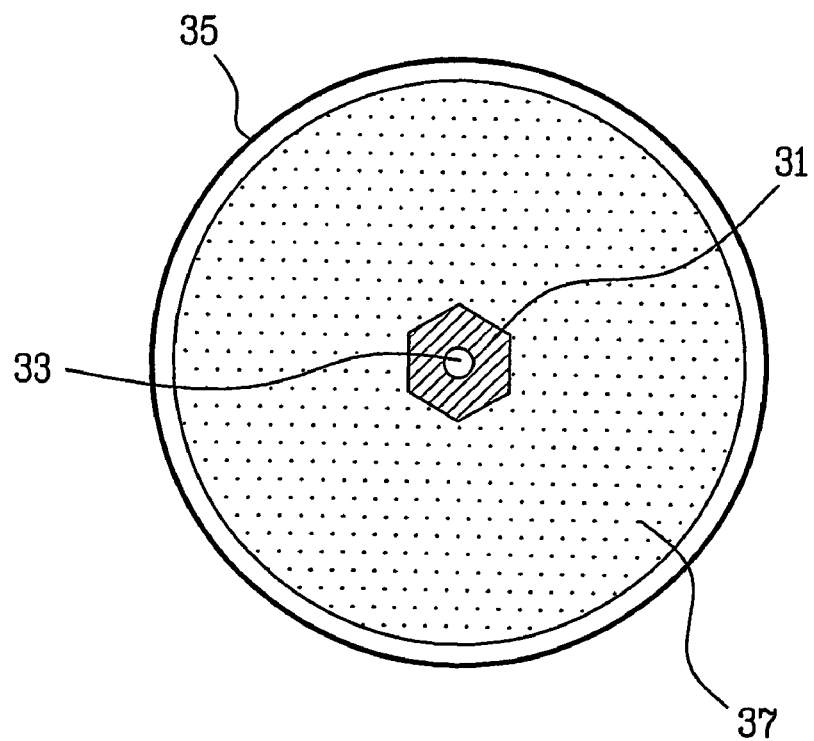

Referring to FIGS. 3A and 3B, another embodiment of the current injecting device 100 of the present invention includes an electrode 31, a wire 33 connected to the electrode 31, an semispherical insulating container 35 having the electrode 31 attached thereto. The insulating container 35 has one side having the electrode 31 attached thereto, and the other surface to be brought into contact with the measuring object 'S' in an opened state. The insulating container 35 is stuffed with sponge 37 having the electrolyte gel or electrolyte solution absorbed therein. The sponge 37 may be replaced by only the electrolyte gel.

The current injecting devices 100 are attached to a circumference of the measuring object 'S', and the current is made to flow only to one pair of the current injecting devices 100 at a time, such that the current flows through the inside of the measuring object 'S' with the one pair of the current injecting devices 100. If it is assumed that a number of the current injecting devices 100 is 'E', a number 'N' of cases of the pairs of the current injecting devices 100 for injecting the current into the measuring object 'S' is $E(E-1)/2$. This is equal to a number of current paths in the measuring object 'S'. A current between the pair of current injecting devices 100 is represented with $I^j$ ($j=1, 2, ---, N$). The current $I^j$ forms a current density $J^j$ ($J^j x, J^j y, J^j z$) in the measuring object 'S'.

The MRI scanner 200 measures a magnetic flux density $B^j$ in the measuring object 'S' due to the current $I^j$, particularly, a z-directional magnetic flux density $B^j z$ parallel to a main magnetic field of the MRI scanner 200. That is, the MRI scanner 200 measures magnetic flux densities $B^1 z$, $B^2 z$, $B^3 z$, ---, $B^N z$ due to currents $I^1, I^2, I^3, ---, I^N$ injected into the measuring object 'S', respectively.

The operating part 300 selects one of the pairs of the current injecting devices 100 in succession, and controls the one of the pair of the current injecting devices to inject the current into the measuring object 'S'. The operating part 300 also applies the magnetic flux density $B^j z$ measured by the MRI scanner 200 to a preset algorithm, and calculates a conductivity σ and a current density $J^j$ inside of the measuring object 'S'. Since the conductivity σ is an inversion of the resistivity ρ, the resistivity ρ can be represented with 1/σ. Then, the displaying means 400 visualizes the inside of the measuring object 'S' according to the conductivity σ and the current density $J^j$.

A method for visualizing conductivity and current density distributions in accordance with a preferred embodiment of the present invention, and an algorithm applied thereto will be described, in detail.

First Embodiment

Referring to FIG. 1, a plurality of current injecting devices 100 are attached to a circumference of a measuring object 'S', i.e., a human body, and the measuring object 'S' is placed in an MRI scanner 200. In this instance, as described before, an insulating container 25 of the current injecting device 100 is stuffed with sponge having electrolyte gel or electrolyte solution absorbed therein.

Figure 4A:
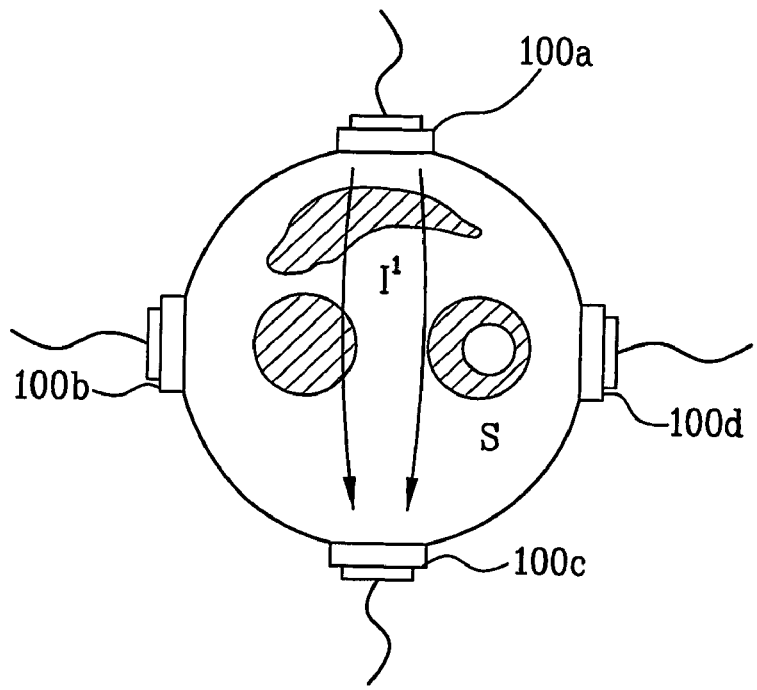
FIGS. 4A and 4B illustrate diagrams each showing a current flow in the measuring object.
Figure 4B:
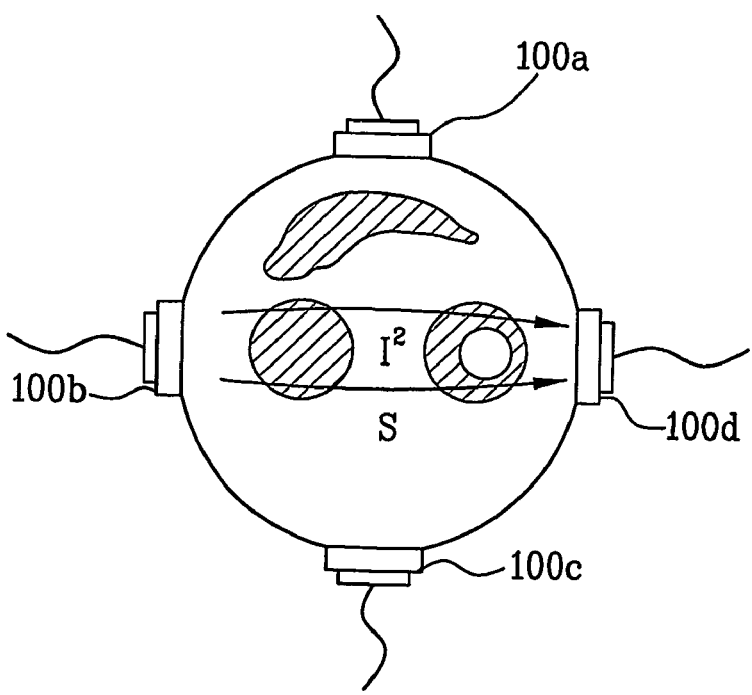

Pairs of the current injecting devices 100 are selected one by one in succession, and a current $I^j$ (j=1, 2, - - - , N) is supplied to an inside of the measuring object 'S' through the pair of the current injecting device 100 selected in succession. For an example, as shown in FIGS. 4A and 4B, in a case four current injecting devices 100a, 100b, 100c, and 100d are attached to a circumference of the measuring object 'S', the currents are supplied to the inside of the measuring object 'S' in two directions in succession. At first, a current $I^1$ is supplied from the current injecting device 100a to the current injecting device 100c, and then, a current $I^2$ is supplied from the current injecting device 100b to the current injecting device 100d. In these instances, the MRI scanner 200 measures the magnetic flux densities $B^1z$ and $B^2z$ due to the currents $I^1$ and $I^2$ injected into the measuring object 'S' respectively. The MRI scanner 200 measures 'z' direction components of the magnetic flux densities, only.

Then, the operating part 300 applies the magnetic flux densities $B^1z$ and $B^2z$ measured by the MRI scanner 200 and voltages $V^j|_{\partial S}$ due to the currents $I^1$ and $I^2$ at a surface of the measuring object 'S' to a preset algorithm, and calculates the conductivity σ and the current density $J^j$ inside of the measuring object 'S'.

Equations to be used for the algorithm in the first embodiment will be described, where, S: a measuring object,
∂S: a surface of the measuring object,
$g^j$: a component of a current density of an injected current at a surface of the measuring object,
n: a unit normal vector at the surface of the measuring object,
$V^j$: a voltage of the injected current in the measuring object.

A relation between the current density $J^j=(J^jx, J^jy, J^jz)$ and the magnetic flux density $B^j=(B^jx, B^jy, B^jz)$ can be expressed as the following equation (1) according to the Ampere's law $$J^j = \frac{1}{\mu_0} \nabla \times B^j.$$

$$-\partial x J^j y + \partial y J^j x = \frac{1}{\mu_0}(\partial^2 x + \partial^2 y + \partial^2 z)B^j z = \frac{1}{\mu_0}\Delta B^j z \quad (1)$$

The equation (1) expresses a relation between the current density $J^j$ and the magnetic flux density $B^j z$ inside of the measuring object. In this instance, of the magnetic flux density $B^j$, only a 'z' direction magnetic flux component $B^j z$ is taken into account.

$$J^j \cdot n = -\sigma \nabla V^j \cdot n = g^j \quad (2)$$

The equation (2) expresses a relation between the current density and the surface voltage at a surface of the measuring object 'S'.

The current density $J^j$ can be expressed as the following equation (3).

$$J^j = -\sigma \nabla V^j \quad (3)$$

Once the conductivity and the voltage inside of the measuring object are calculated, the current density of the injected current can be calculated by the equation (3). If equation (3) is substituted into a left side of the equation (1), the following equation (4) is obtained.

$$\partial x \sigma \partial y V^j - \partial y \sigma \partial x V^j = \frac{1}{\mu_0}\Delta B^j z \quad (4)$$

The equation (4) expresses a relation between the voltage and the current density inside of the measuring object 'S'. As shown in FIGS. 4A and 4B, when two currents $I^1$ and $I^2$ are injected into the measuring object 'S' in different directions, the relation between the voltage and the current density inside of the measuring object 'S' can be expressed as follows.

$$\begin{pmatrix} \partial y V^1 & -\partial x V^1 \\ \partial y V^2 & -\partial x V^2 \end{pmatrix} \begin{pmatrix} \partial x \sigma \\ \partial y \sigma \end{pmatrix} = \begin{pmatrix} \frac{1}{\mu_0}\Delta B_z^1 \\ \frac{1}{\mu_0}\Delta B_z^2 \end{pmatrix} \quad (5)$$

In a case the two currents $I^1$ and $I^2$ are supplied to the measuring object 'S' through two pairs of the current injecting devices 100, if the current densities due to the two currents $I^1$ and $I^2$ satisfy the following equation (6), the conductivity σ can be obtained.

$$\begin{vmatrix} -J_y^1 & J_x^1 \\ -J_y^2 & J_x^2 \end{vmatrix} \neq 0 \quad (6)$$

Since the currents $I^1$ and $I^2$ of different directions are injected into the measuring object 'S', the current densities due to the two currents $I^1$ and $I^2$ have different directions in almost all regions of the inside of the measuring object 'S'. Therefore, the equation (6) is satisfied in all positions of the measuring objects 'S'.

If an inverse matrix of the equation (5) is taken, the following equations (7) can be obtained.

$$\partial x \sigma = \frac{\partial x V^2 \Delta B_z^1 - \partial x V^1 \Delta B_z^2}{\mu_0(\partial y V^1 \partial x V^2 - \partial x V^1 \partial y V^2)}, \text{ and} \quad (7)$$

$$\partial y \sigma = \frac{\partial y V^2 \Delta B_z^1 - \partial x V^1 \Delta B_z^2}{\mu_0(\partial y V^1 \partial x V^2 - \partial x V^1 \partial y V^2)}$$

Since the current density satisfies an equation $\partial_x J_x^j + \partial_y J_y^j + \partial_z J_z^j = 0$, the following equations (8) can be derived from the equations (7).

$$\nabla \cdot ((\sigma(x_0,y_0,z)+F[V^1,V^2,B_Z^1,B_Z^2])\nabla V^1)=0,$$

$$\nabla \cdot ((\sigma(x_0,y_0,z)+F[V^1,V^2,B_Z^1,B_Z^2])\nabla V^2)=0,$$

$$(\sigma(x_0,y_0,z)+F[V^1,V^2,B_Z^1,B_Z^2])\nabla V^1 \cdot n_{aS}=-g^1,$$

$$(\sigma(x_0,y_0,z)+F[V^1,V^2,B_Z^1,B_Z^2])\nabla V^2 \cdot n_{aS}=-g^2,$$

$$\int_{aS} V^1=0, \text{ and } \int_{aS} V^2=0 \quad (8)$$

In the equations (8), the first and second equations are ones for the inside of the measuring object 'S', and rest of the equations (8) are ones for the surface of the measuring object 'S'. $F[V^1,V^2,B_Z^1,B_Z^2]$ can be expressed as follows.

$$F[V^1, V^2, B_z^1, B_z^2] = \int_{x_0}^{x} \frac{\partial xV^2 \Delta B_z^1 - \partial xV^1 \Delta B_z^2}{\mu_0 \left( \begin{array}{c} \partial yV^1 \partial xV^2 - \\ \partial xV^1 \partial yV^2 \end{array} \right)}(t, y_0, z)dt +$$
$$\int_{y_0}^{y} \left( \frac{\partial yV^2 \Delta B_z^1 - \partial yV^1 \Delta B_z^2}{\mu_0(\partial yV^1 \partial xV^2 - \partial xV^1 \partial yV^2)} \right)(x, t, z)dt$$

The algorithm of the first embodiment calculates the conductivity $\sigma$ and the current density $J$ of an inside of the measuring object 'S' by using the foregoing equations. A process for calculating the conductivity $\sigma$ and the current density $J$ of an inside of the measuring object 'S' by applying the magnetic flux densities $B^1z$ and $B^2z$, and the voltages $V_j|_{aS}$ due to the currents $I^1$ and $I^2$ at a surface of the measuring object 'S' to a preset algorithm, in detail.

An initial conductivity $\sigma_0$ is set to unity or any desired value, and by substituting the initial conductivity $\sigma_0$ and the current density component $gj$ at the surface of the measuring object 'S' into the following equations (9), initial voltages $V_0^1$ and $V_0^2$ induced at the measuring object 'S' by the injected currents $I^1$ and $I^2$ can be obtained. The initial voltages $V_0^1$ and $V_0^2$ are calculated by using the FEM or FDM in solving a partial differential equation, which are voltages for the initial conductivity $\sigma_0$ set as desired.

$$\nabla \cdot (\sigma_0(x,y,z)\nabla V_0^1)=0,$$

$$\sigma_0(x,y,z)\nabla V_0^1 \cdot n|_{aS}=-g^1, \text{ and}$$

$$\int_{aS} V^1=0, \text{ and}$$

$$\nabla \cdot (\sigma_0(x,y,z)\nabla V_0^2)=0,$$

$$\sigma_0(x,y,z)\nabla V_0^2 \cdot n|_{aS}=-g^2, \text{ and}$$

$$\int_{aS} V^2=0 \quad (9)$$

The initial voltages $V_0^1$ and $V_0^2$ calculated by using the equations (9), and the measured magnetic flux densities $B_z^1$ and $B_z^2$ are substituted into the following equations (10), to calculate voltages $V_1^1$ and $V_1^2$.

$$\nabla \cdot ((\sigma(x_0,y_0,z)+F[V_0^1,V_0^2,B_Z^1,B_Z^2])\nabla V_1^1)=0,$$

$$\nabla \cdot ((\sigma(x_0,y_0,z)+F[V_0^1,V_0^2,B_Z^1,B_Z^2])\nabla V_1^2)=0,$$

$$(\sigma(x_0,y_0,z)+F[V_0^1,V_0^2,B_Z^1,B_Z^2])\nabla V_1^1 \cdot n_{aS}=-g^1,$$

$$(\sigma(x_0,y_0,z)+F[V_0^1,V_0^2,B_Z^1,B_Z^2])\nabla V_1^2 \cdot n_{aS}=-g^2,$$

$$\int_{aS} V_1^1=0, \text{ and } \int_{aS} V_1^2=0 \quad (10)$$

Herein, $\sigma(x_0,y_0,z)+F[V_0^1,V_0^2,B_Z^1,B_Z^2]$, a value of the second conductivity $\sigma_1$, can be obtained by using the initial voltages $V_0^1$ and $V_0^2$, and the measured magnetic flux densities $B_z^1$ and $B_z^2$. The second conductivity $\sigma_1$ is closer to a true conductivity than the initial conductivity $\sigma_0$, because the calculated conductivity $\sigma_1$ has taken true magnetic flux densities $B_z^1$ and $B_z^2$ of the inside of the measuring object 'S' into account.

Then, the calculated voltages $V_1^1$ and $V_1^2$, and the measured magnetic flux densities $B_z^1$ and $B_z^2$ are substituted into the following equations (11), to calculate voltages $V_2^1$ and $V_2^2$. Herein, $\sigma(x_0,y_0,z)+F[V_1^1,V_1^2,B_Z^1,B_Z^2]$, a value of the third conductivity $\sigma_2$, can be obtained by using the calculated voltages $V_1^1$ and $V_1^2$, and the measured magnetic flux densities $B_z^1$ and $B_z^2$. The third conductivity $\sigma_2$ is closer to the true conductivity than the conductivities $\sigma_0$ and $\sigma_1$.

Hereafter, by using the voltages $V_2^1$ and $V_2^2$, a fourth conductivity $\sigma_3$ and the next stage voltages may be calculated.

$$\nabla \cdot ((\sigma(x_0,y_0,z)+F[V_1^1,V_1^2,B_Z^1,B_Z^2])\nabla V_2^1)=0,$$

$$\nabla \cdot ((\sigma(x_0,y_0,z)+F[V_1^1,V_1^2,B_Z^1,B_Z^2])\nabla V_2^2)=0,$$

$$(\sigma(x_0,y_0,z)+F[V_1^1,V_1^2,B_Z^1,B_Z^2])\nabla V_2^1 \cdot n_{aS}=-g^1,$$

$$(\sigma(x_0,y_0,z)+F[V_1^1,V_1^2,B_Z^1,B_Z^2])\nabla V_2^2 \cdot n_{aS}=-g^2,$$

$$\int_{aS} V_2^1=0, \text{ and } \int_{aS} V_2^2=0 \quad (11)$$

As described, for obtaining a conductivity close to a true value, values up to $V^1_{m+1}$ and $V^2_{m+1}$ are obtained from the initial voltages $V_0^1$ and $V_0^2$ by using an iterative algorithm. The calculation for obtaining the voltage values are repeated until the following equation (12) is satisfied.

$$|V^1_{m+1}-V^1_m|<\alpha_1, \text{ and}$$

$$|V^2_{m+1}-V^2_m|<\alpha_2, (m=0, 1, 2, 3, \cdots .) \quad (12)$$

In other words, differences between the voltages at an (m)th step and the voltages at an (m+1)th step are calculated, and it is determined whether the differences are smaller than $\alpha_1$ and $\alpha_2$, respectively. If the differences are greater than preset values respectively, the voltage calculation process is repeated. Opposite to this, if the calculated differences are smaller than the preset values respectively, the values of the $V^1_m$ and $V^2_m$ are substituted into the following equation (13), to calculate a conductivity $\sigma_{m+1}$.

$$\sigma = \lim_{m \to \infty} \sigma^m = \lim_{m \to \infty} (\sigma(x_0, y_0, z) + F[V_m^1, V_m^2, B_z^1, B_z^2]) \quad (13)$$

Even though 'm' approaches to infinitive in the equation (13), it is required that the 'm' is set to an appropriate value. The 'm' in the equation (13) increases until the difference of calculated conductivity satisfies a condition $\sigma_{m+1}-\sigma_m<\epsilon$. The $\epsilon$ is a set value.

Then, a voltage corresponding to the calculated conductivity $\sigma_{m+1}$ is calculated by using the following equation (14).

$$\nabla \cdot (\sigma \nabla V^1)=0,$$

$$\sigma \nabla V^1 \cdot n|_{aS}=-g^1, \text{ and}$$

$$\int_{aS} V^1=0, \text{ and}$$

$$\nabla \cdot (\sigma \nabla V^2)=0,$$

$$\sigma \nabla V^2 \cdot n|_{aS}=-g^2, \text{ and}$$

$$\int_{aS} V^2=0, \text{ and}$$

Then, the voltages calculated by the equation (14) are substituted into the following equation (15), to calculate current densities. Then, by using the calculated conductivity $\sigma_{m+1}$ or the current density, the inside of the measuring object can be visualized.

$$J^1 = -\sigma \nabla V^1, \text{ and}$$

$$J^2 = -\sigma \nabla V^2 \tag{15}$$

Second Embodiment

A plurality of current injecting devices 100 are attached to a circumference of a measuring object 'S', i.e., a human body, and the measuring object 'S' is placed in an MRI scanner 200. In this instance, as described before, an insulating container of the current injecting device 100 is stuffed with sponge having electrolyte gel or electrolyte solution absorbed therein.

Figure 5:
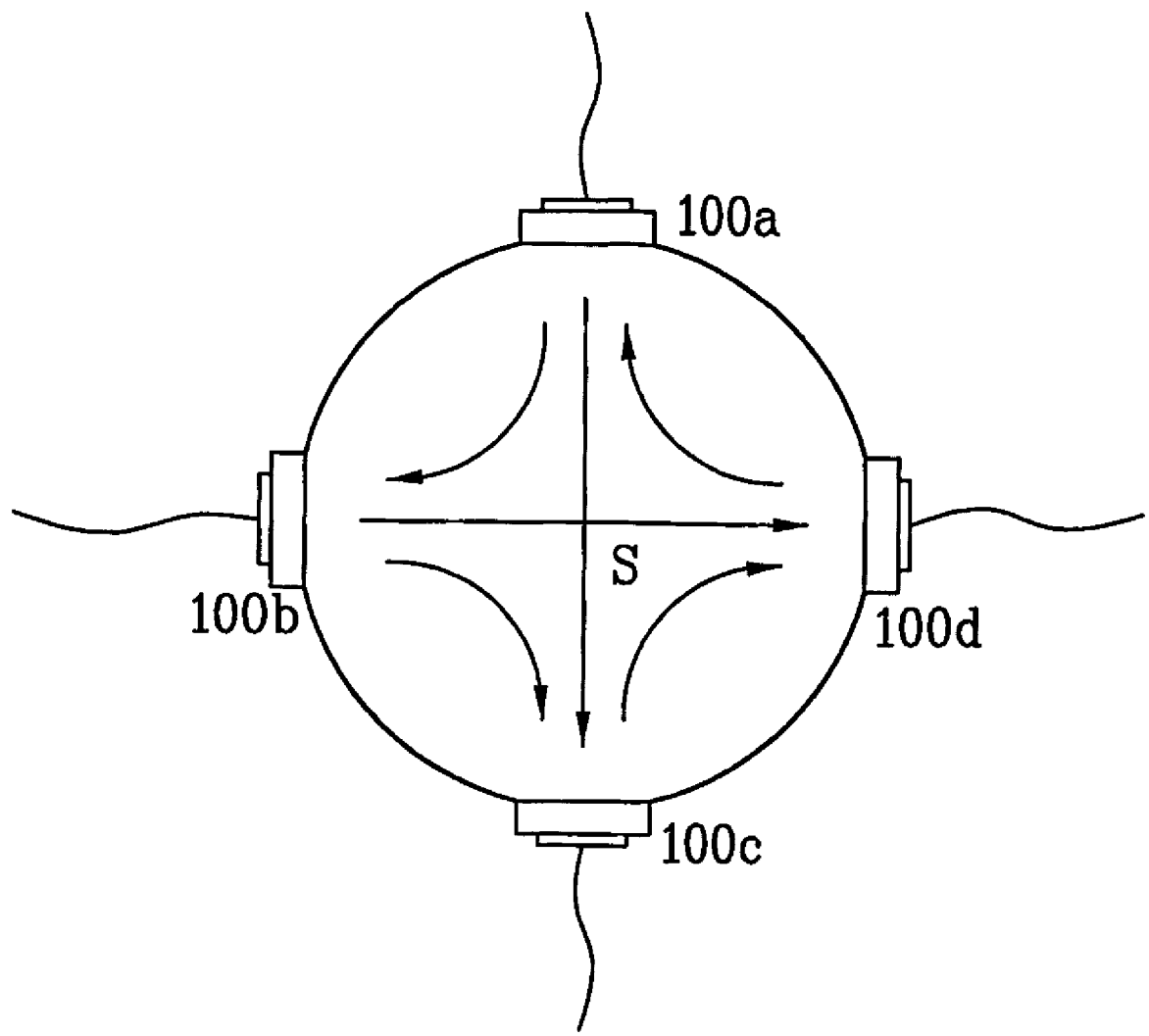
FIG. 5 illustrates a diagram showing another form of current flows in the measuring object.

Pairs of the current injecting devices 100 are selected one by one in succession, and a current $I^j$ (j=1, 2, - - -, N) is supplied to an inside of the measuring object 'S' through the pair of the current injecting device 100 selected in succession. For an example, as shown in FIG. 5, in a case four current injecting devices 100a, 100b, 100c, and 100d are attached to the circumference of the measuring object 'S', the current injecting devices can be paired in six cases for injecting the currents, such that the currents flow in six paths, and in six directions respectively under the control of the operating part 300. The currents of the six paths are a current $I^1$ between the current injecting devices 100a and 100c, a current $I^2$ between the current injecting devices 100b and 100d, a current $I^3$ between the current injecting devices 100a and 100b, a current $I^4$ between the current injecting devices 100b and 100c, a current $I^5$ between the current injecting devices 100c and 100d, and a current $I^6$ between the current injecting devices 100d and 100a. In these instances, the MRI scanner 200 measures the magnetic flux densities $B^1z, B^2z, ---, B^6z$ due to the currents $I^1, I^2, ---, I^6$ injected into the measuring object 'S' respectively. The MRI scanner 200 measures 'z' direction components of the magnetic flux densities, only.

Then, the operating part 300 applies the magnetic flux densities $B^1z, B^2z, ---, B^6z$ measured by the MRI scanner 200 and voltages $V^j|_{\partial S}$ due to the currents $I^1, I^2, ---, I^6$ at a surface of the measuring object 'S' to a preset algorithm, and calculates the conductivity $\sigma$ and the current density $J^j$ inside of the measuring object 'S'.

Equations to be used for the algorithm in the second embodiment will be described.

It is assumed that the conductivity C inside of the measuring object 'S' is isotropic within a range $0<\sigma<\infty$. Since the conductivity $\sigma$ is not relevant to the current substantially, the voltages $V^j$ can be obtained from the following equation (16).

$$\nabla \cdot (\sigma \nabla V^j) = 0, \text{ and}$$

$$\sigma \nabla V^j \cdot n = -g^j \ (j=1, 2, 3, ---, N) \tag{16}$$

The current density $g^j$ is zero (0) at the surface of the measuring object 'S' not in contact with the selected pair of the current injecting devices 100. If the conductivity $\sigma$, the injected current $I^j$, and positions of the current injecting devices 100 are known, the voltage $V^j$ can be calculated by a calculating method, such as FEM.

Moreover, an equation $\nabla^2 B = -\mu_0 \nabla V \times \nabla \sigma$ can be derived from the Ampere's law. If a z component of the equation is expressed with respect to a position of the inside of the measuring object 'S', the following equation (17) is obtained.

$$\frac{1}{\mu_0} \nabla^2 B_z^j = \left( \frac{\partial V^j}{\partial y}, -\frac{\partial V^j}{\partial x} \right) \cdot \left( \frac{\partial \sigma}{\partial x}, \frac{\partial \sigma}{\partial y} \right) \tag{17}$$

Where, $\mu_0$ is a magnetic permeability in the free space. The equation (17) can be expressed in a matrix form as the following equation (18).

$$\frac{1}{\mu_0} \begin{bmatrix} \nabla^2 B_z^1 \\ \vdots \\ \nabla^2 B_z^N \end{bmatrix} = \begin{bmatrix} \frac{\partial V^1}{\partial y} & -\frac{\partial V^1}{\partial x} \\ \vdots & \vdots \\ \frac{\partial V^N}{\partial y} & -\frac{\partial V^N}{\partial x} \end{bmatrix} \begin{bmatrix} \frac{\partial \sigma}{\partial x} \\ \frac{\partial \sigma}{\partial y} \end{bmatrix} \tag{18}$$

If $\frac{1}{\mu_0} \begin{bmatrix} \nabla^2 B_z^1 \\ \vdots \\ \nabla^2 B_z^N \end{bmatrix}$ is set to be 'b', $$\begin{bmatrix} \frac{\partial V^1}{\partial y} & -\frac{\partial V^1}{\partial x} \\ \vdots & \vdots \\ \frac{\partial V^N}{\partial y} & -\frac{\partial V^N}{\partial x} \end{bmatrix}$$

is set to be 'U', and $$\begin{bmatrix} \frac{\partial \sigma}{\partial x} \\ \frac{\partial \sigma}{\partial y} \end{bmatrix}$$

is set to be 's', the equation (18) can be expressed as b=Us.

If two currents $I^1$ and $I^2$ are supplied to the measuring object 'S' through two pairs of the current injecting devices 100, if two voltages V1 and V2 due to the two currents $I^1$ and $I^2$ satisfies the following equation (19), above matrix equation can be solved.

$$-\frac{\partial V^1}{\partial y} \frac{\partial V^2}{\partial x} + \frac{\partial V^1}{\partial x} \frac{\partial V^2}{\partial y} \neq 0 \tag{19}$$

Since the two current densities $J^1$ and $J^2$ due to the two currents $I^1$ and $I^2$ have directions different from each other in almost all regions of the inside of the measuring object 'S', the equation (19) can be satisfied in all positions of the measuring object 'S'.

The equation (18) can be expressed as the following equation (20) by using weighted regularized least square method.

$$s = (\overline{U}^T \overline{U} + \lambda I)^{-1} \overline{U}^T \overline{b} \tag{20}$$

Where, $U^T$ denotes a transpose of 'U', and $\overline{U}=WU$, $\overline{b}=Wb$, $W=\text{diag}(w_1, w_2, ---, w_N)$. W denotes an N×N matrix, I denotes a 2×2 unit matrix. λ denotes a positive regularization parameter. The weighting factor $w_j$ is set as the following equation (21).

$$w_j = \frac{SNR_j}{\sum_{j=1}^{N} SNR_j} \quad (21)$$

The SNR denotes a signal-to-noise ratio of the magnetic flux density $B^j_z$ measured by the MRI scanner 200. By adjusting the weighting factor $w_j$ according to the noise of the magnetic flux density $B^j_z$, a more accurate 's' value can be obtained.

If the equation (20) is calculated for all positions of inside of the measuring objects 'S', a distribution of $$s = \left[\frac{\partial \sigma}{\partial x} \frac{\partial \sigma}{\partial y}\right]^T$$

inside of the measuring object 'S' can be known.

For displaying the three dimensional (or solid) measuring object 'S' on a two dimensional screen, it is required to fix one of the three dimensions. Therefore, when it is intended to display a two dimensional image for convenience, it is assumed that z=0. It is also assumed that the conductivity at a fixed position $r_0=(x_0, y_0, 0)$ at the surface $\partial S$ is unity. There are two methods for calculating the conductivity from $$\nabla \sigma = \left(\frac{\partial \sigma}{\partial x}, \frac{\partial \sigma}{\partial y}\right).$$

One is the line integral method, and the other is the layer potential method.

The line integral method is the same with the method suggested in the first embodiment, in which the following equation (22) can be used.

$$\sigma(x,y) = \sigma(x_0, y_0) + \int_{x_0}^{x} \frac{\partial \sigma}{\partial x}(x, y_0)dx + \int_{y_0}^{y} \frac{\partial \sigma}{\partial y}(x, y)dy \quad (22)$$

Where, $\sigma(x_0, y_0)$ is set to unity.

The layer potential method uses the following equation (23).

$$\sigma(r) = \int_S \nabla^2 \Phi(r-r')\sigma(r')dr' \quad (23)$$
$$= -\int_S \nabla_{r'} \Phi(r-r') \cdot \nabla \sigma(r')dr' +$$
$$\int_{\partial S'} n_{r'} \cdot \nabla_{r'} \Phi(r-r')\sigma(r')dl_{r'}$$

Where, $$\Phi(r-r') = \frac{1}{2\pi}\log|r-r'|, \text{ and}$$

$$\nabla_{r'}\Phi(r-r') = -\frac{1}{2\pi}\frac{r-r'}{|r-r'|^2}.$$

The following equation (24) can be derived with respect to the surface $\partial S$ of the measuring object 'S'.

$$\lim_{t \to +0}\int_{\partial S} n_{r'} \cdot \nabla_{r'} \Phi(r - tn_r - r')\sigma(r')dl_{r'} = \quad (24)$$
$$\frac{\sigma(r)}{2} + \int_{\partial S} n_{r'} \cdot \nabla_{r'} \Phi(r-r')\sigma(r')dl_{r'}$$

Moreover, the following equation (25) can be derived from equation (23).

$$\frac{\sigma_{\partial S}(r)}{2} - \frac{1}{2\pi}\int_{\partial S}\frac{(r-r') \cdot n_{r'}}{|r-r'|^2}\sigma_{\partial S}(r')dl_{r'} = \frac{1}{2\pi}\int_S \frac{(r-r') \cdot \nabla \sigma(r')}{|r-r'|^2}dr' \quad (25)$$

Where, $\sigma_{\partial S}$ denotes the conductivity limited to $\partial S$ of the measuring object 'S'. By using the equation (25), a surface conductivity $\sigma_{\partial S}$, i.e., the conductivity at a surface $\partial S$ of the measuring object 'S' can be obtained. By substituting the surface conductivity $\sigma_{\partial S}$ into equation (23), the conductivity σ of the inside of the measuring object 'S' can be obtained. By substituting the surface conductivity $\sigma_{\partial S}$ into equation (23), the following equation (26) can be obtained.

$$\frac{\sigma(r)}{2} = \quad (26)$$
$$-\int_S \nabla_{r'}\Phi(r-r') \cdot \nabla\sigma(r')dr' + \int_{\partial S} n_{r'} \cdot \nabla_{r'}\Phi(r-r')\sigma_{\partial S}(r')dl_{r'}$$

The equations (18), (22), and (26) can be repeated with respect to all regions of the measuring object 'S'.

If the magnetic flux density $B^j_z$ measured by the MRI scanner 200 is substituted into the equation (18), the 's', i.e., $\nabla\sigma$ can be derived. However, if the voltage $V^j$ inside of the measuring object 'S' is not known, a true conductivity σ inside of the measuring object 'S' can not be obtained. Therefore, an initial conductivity $\sigma_0$ is assumed, to calculate the voltage $V^j$ inside of the measuring object 'S', and conductivity $\sigma_m$ is calculated repeatedly until the conductivity $\sigma_m$ approaches close to a true conductivity. In order to solve a problem in which the conductivity $\sigma_m$ differs from the true conductivity by a multiplication of a constant, the surface voltages $V^j|_{\partial S}$ due to the injected voltage $I^j$ is used. The surface voltages $V^j|_{\partial S}$ are voltages at surfaces between the current injecting devices 100 that are not selected and the measuring object 'S', when the current is supplied to the measuring object 'S' through the pair of the current injecting devices 100. The surface voltages $V^j|_{\partial S}$ are measured with the current injecting devices 100 that are not selected.

A process for calculating the conductivity and the current density at the operating part 300 by applying the measured conductivity $B^j$, and the measured surface voltages $V^j|_{\partial S}$ to the foregoing equations will be described in detail.

The initial conductivity $\sigma_m$ (m=0) is set, and the initial conductivity $\sigma_m$ (m=0) and the current density component g at the surface of the measuring object 'S' are substituted into the following equation (27), to calculate voltages $V^j_{m+1}$ and $V_{j_{m+1}}|_{\partial S}$ at the inside and the surface of the measuring object 'S'. Those are voltages for the initial conductivity set as desired. The current density component $g^j$ can be known from the current $I^j$ (j=1, 2, ---, N).

$$\nabla \cdot (\sigma \nabla V^j_{m+1}) = 0, \text{ and}$$
$$\sigma \nabla V^j_{m+1}|_{\partial S} \cdot n = -g^j \; (j=1, 2, 3, ---, N) \quad (27)$$

After the voltage $V^j_{m+1}$ inside of the measuring object 'S' for the initial conductivity is obtained, the voltage $V^j_{m+1}$ and the measured magnetic flux density $B^j_z$ are substituted into the equation (18), and the equation (22), or equation (26) is used, to calculated the conductivity $\sigma_{m+1}$. The calculated conductivity $\sigma_{m+1}$ is closer to a true conductivity than the conductivity $\sigma_m$, because the calculated conductivity $\sigma_{m+1}$ has taken an true magnetic flux density $B^j_z$ inside of the measuring object 'S' into account.

However, even if the calculated conductivity $\sigma_{m+1}$ has taken the true magnetic flux density $B^j_z$ into account, the calculated conductivity $\sigma_{m+1}$ can differ from the true conductivity. That is, though the calculated conductivity $\sigma_{m+1}$ has a value varied with the magnetic flux density $B^j_z$, the calculated conductivity $\sigma_{m+1}$ may be greater or smaller than the true conductivity by a multiplication of a constant. For eliminating the difference caused by the multiplication of the constant of the calculated conductivity $\sigma_{m+1}$ from the true conductivity, in the present invention, the measured surface voltage $V^j|_{\partial S}$ and the calculated surface voltage $V_{m+1}{}^j|_{\partial S}$ are used for scaling the conductivity $\sigma_{m+1}$. In other words, according to a ratio of the measured surface voltage $V^j|_{\partial S}$ to the calculated surface voltage $V_{m+1}{}^j|_{\partial S}$, the conductivity $\sigma_{m+1}$ is multiplied or divided by a constant value.

Moreover, in the present invention, for obtaining the conductivity close to the true value, an iterative form of algorithm is used. That is, alike the following equation $\|\sigma_{m+1} - \sigma_m\| < \epsilon$, a difference between a conductivity $\sigma_m$ in a prior step and a conductivity cut, in the present step is calculated, and it is determined whether an absolute value of the difference is smaller than a preset value '$\epsilon$' or not. The equation (27) is calculated repeatedly by increasing the 'm' until the calculated difference becomes smaller than the preset value 'e'.

If the absolute value of the difference of the conductivity $\sigma_m$ in the prior step and the conductivity $\sigma_{m+1}$ in the present step is smaller than the preset value '$\epsilon$', the conductivity $\sigma_{m+1}$ is taken as the true conductivity, by using the conductivity $\sigma_{m+1}$, the measuring object 'S' is visualized.

Then, the conductivity $\sigma_{m+1}$ is substituted into the equation (16) to calculated a voltage for the conductivity $\sigma_{m+1}$, i.e., the true voltage $V^j$ inside of the measuring object 'S' is calculated. Then, by using the conductivity $\sigma_{m+1}$ and the voltage $V^j$, the current density $J^j$ is calculated, and by using the current density $J^j$, the inside of the measuring object 'S' is visualized.

INDUSTRIAL APPLICABILITY

As has been described, the present invention permits to obtain a conductivity distribution image and a current density distribution image of an inside of a measuring object without rotating the measuring object, such as a human body, or a substance, within an MRI scanner.

Moreover, by using the current injecting devices together with the present MRI scanner, the conductivity distribution image and the current density distribution image of the inside of the measuring object are made available, that have not been available only with the present MRI scanner, and by using which a high quality image can be reproduced.

Furthermore, the conductivity distribution image and the current density distribution image can be applicable to the present medical equipment. According to this, a functional imaging can be provided for organs each of which biological tissue conductivity varies with physiologic action, to secure a new medical examination technology. For an example, an image required for measuring a volume of a lung varies with respiration (a measurement by using variation of a resistivity of the lung in inhale and exhale of air), a measurement of an cardiac output of a heart, a measurement of a stomach, a measurement of cystic residual urine, a measurement of a healed state of a bone fracture, or a measurement of a brain function.

Since quantitative electric properties of a human tissue can be known, optimization of diagnosis equipments, and treatment equipments using electro-magnetic energy, such as various electric/magnetic stimulators, defibrillators, cardiac pacemakers, and the like, is made possible.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A system for visualizing conductivity and current density distributions comprising:
   a plurality of current injecting devices for injecting currents into a measured object;
   an MRI scanner for measuring one directional component of a magnetic flux density due to each of the currents injected into the measured object;
   an operating part for controlling the current injecting devices so as to inject currents of different directions into the measured object, and calculating a conductivity distribution and a current density distribution inside of the measured object by using the one directional component of a magnetic flux density wherein the operating part calculates an inside voltage and a surface voltage of the measured object for a discretionary conductivity, and calculates the conductivity distribution by using the calculated inside voltage and the one directional component of the magnetic flux density; and
   displaying means for visualizing the conductivity distribution and current density distributions calculated by the operating part.

2. The system as claimed in claim 1, wherein the current injecting device includes;
   an electrode,
   an insulating container with the electrode attached to one side, the insulating container having an electrolyte substance, and
   a wire for supplying the current to the electrode.

3. The system as claimed in claim 1, wherein the operating part controls the current injecting devices such that one pair of the current injecting devices are selected in succession, and the selected pair of the current injecting devices supply the current to the measured object.

4. The system as claimed in claim 1, wherein the operating part multiplies or divides a constant to the conductivity distribution according to a ratio of the calculated surface voltage to a measured surface voltage.

5. The system as claimed in claim 1, wherein, if an absolute value of a difference of the discretionary conductivity and the conductivity distribution is greater than a preset value, the operating part calculates a inside voltage and a surface voltage for the conductivity distribution, and calculates a new conductivity distribution by using the inside voltage for the second conductivity and the one directional component of the magnetic flux density.

6. The system as claimed in claim 1, wherein the operating part determines that the conductivity distribution is a true conductivity, if the absolute value of the difference of the discretionary conductivity and the conductivity distribution is smaller than the present value.

7. The system as claimed in claim 1, wherein the operating part substitutes the inside voltage and the one direction component of the magnetic flux density into the following equation, and subjects the equation to a line integral, to obtain the second conductivity distribution:

$$\frac{1}{\mu_0}\begin{bmatrix} \nabla^2 B_z^1 \\ \vdots \\ \nabla^2 B_z^N \end{bmatrix} = \begin{bmatrix} \frac{\partial V^1}{\partial y} & -\frac{\partial V^1}{\partial x} \\ \vdots & \vdots \\ \frac{\partial V^N}{\partial y} & -\frac{\partial V^N}{\partial x} \end{bmatrix} \begin{bmatrix} \frac{\partial \sigma}{\partial x} \\ \frac{\partial \sigma}{\partial y} \end{bmatrix}$$

Where, $\mu_o$ denotes a magnetic permeability of the free space.

8. The system as claimed in claim 1, wherein the operating part substitutes the inside voltage and the one directional component of the magnetic flux density into the following equation, and solves the equation by layer potential method, to obtain the second conductivity distribution:

$$\frac{1}{\mu_0}\begin{bmatrix} \nabla^2 B_z^1 \\ \vdots \\ \nabla^2 B_z^N \end{bmatrix} = \begin{bmatrix} \frac{\partial V^1}{\partial y} & -\frac{\partial V^1}{\partial x} \\ \vdots & \vdots \\ \frac{\partial V^N}{\partial y} & -\frac{\partial V^N}{\partial x} \end{bmatrix} \begin{bmatrix} \frac{\partial \sigma}{\partial x} \\ \frac{\partial \sigma}{\partial y} \end{bmatrix}$$

Where, $\mu_o$ denotes a magnetic permeability of the free space.

* * * * *